United States Patent
Jarrold et al.

(10) Patent No.: US 11,668,719 B2
(45) Date of Patent: Jun. 6, 2023

(54) METHODS FOR RESOLVING LIPOPROTEINS WITH MASS SPECTROMETRY

(71) Applicant: THE TRUSTEES OF INDIANA UNIVERSITY, Bloomington, IN (US)

(72) Inventors: Martin F. Jarrold, Bloomington, IN (US); Corrine A. Lutomski, Bloomington, IN (US)

(73) Assignee: The Trustees Of Indiana University, Bloomington, IN (US)

( * ) Notice: Subject to any disclaimer, the term of this patent is extended or adjusted under 35 U.S.C. 154(b) by 0 days.

(21) Appl. No.: 16/647,955

(22) PCT Filed: Sep. 20, 2018

(86) PCT No.: PCT/US2018/051944
§ 371 (c)(1),
(2) Date: Mar. 17, 2020

(87) PCT Pub. No.: WO2019/060538
PCT Pub. Date: Mar. 28, 2019

(65) Prior Publication Data
US 2020/0249240 A1 Aug. 6, 2020

Related U.S. Application Data

(60) Provisional application No. 62/561,184, filed on Sep. 20, 2017.

(51) Int. Cl.
*G01N 33/68* (2006.01)
*G01N 33/92* (2006.01)
(Continued)

(52) U.S. Cl.
CPC ........ *G01N 33/6848* (2013.01); *G01N 33/92* (2013.01); *H01J 49/0068* (2013.01);
(Continued)

(58) Field of Classification Search
CPC . G01N 33/6848; G01N 33/92; H01J 49/0068; H01J 49/025; H01J 49/40; H01J 49/425
See application file for complete search history.

(56) References Cited

U.S. PATENT DOCUMENTS 3,019,168 A 1/1962 Taylor
5,285,063 A 2/1994 Schwartz et al.
(Continued)

FOREIGN PATENT DOCUMENTS

WO 1998011244 A1 3/1998
WO 1999061601 A1 12/1999
(Continued)

OTHER PUBLICATIONS

Keifer et al., Charge detection mass spectrometry: weighing heavier things, 142 Analyst 1654 (2017) (Year: 2017).*
(Continued)

*Primary Examiner* — David E Smith
(74) *Attorney, Agent, or Firm* — Barnes & Thornburg LLP

(57) ABSTRACT

The present disclosure relates to a method of identifying components present in a lipoprotein. Methods provided include single particle mass spectrometry, such as charge detection mass spectrometry (CDMS). Distinct subpopulations that exist within lipoprotein classes are determined by correlating m/z and mass.

15 Claims, 6 Drawing Sheets

(51) Int. Cl.
*H01J 49/40* (2006.01)
*H01J 49/42* (2006.01)
*H01J 49/00* (2006.01)
*H01J 49/02* (2006.01)

(52) U.S. Cl.
CPC ............ *H01J 49/025* (2013.01); *H01J 49/40* (2013.01); *H01J 49/4225* (2013.01)

(56) References Cited

U.S. PATENT DOCUMENTS

| | | |
|---|---|---|
| 5,478,745 A | 12/1995 | Samulski |
| 5,572,025 A | 11/1996 | Cotter |
| 5,770,857 A | 6/1998 | Fuerstenau et al. |
| 5,863,541 A | 1/1999 | Samulski et al. |
| 5,869,248 A | 2/1999 | Yuan et al. |
| 5,877,022 A | 3/1999 | Stinchcomb et al. |
| 5,880,466 A | 3/1999 | Benner |
| 5,882,652 A | 3/1999 | Valdes et al. |
| 5,886,346 A | 3/1999 | Makarov |
| 5,905,040 A | 5/1999 | Mazzara et al. |
| 5,916,563 A | 6/1999 | Young et al. |
| 5,965,358 A | 10/1999 | Carrion et al. |
| 6,013,487 A | 1/2000 | Mitchell |
| 6,083,702 A | 7/2000 | Mitchell et al. |
| 6,156,303 A | 12/2000 | Russell et al. |
| 6,183,950 B1 | 2/2001 | Madonna |
| 6,583,408 B2 | 6/2003 | Smith et al. |
| 6,744,042 B2 | 6/2004 | Zajfman et al. |
| 6,753,523 B1 | 6/2004 | Whitehouse |
| 6,888,130 B1 | 5/2005 | Gonin |
| 7,314,912 B1 | 1/2008 | Hallek et al. |
| 7,829,842 B2 | 11/2010 | Makarov |
| 8,294,085 B2 | 10/2012 | Ding |
| 8,395,112 B1 | 3/2013 | Bier |
| 8,409,870 B2 | 4/2013 | Van Wuijckhuijse |
| 9,095,793 B2 | 8/2015 | Flagan |
| 10,056,244 B1 | 8/2018 | Quarmby et al. |
| 2003/0155502 A1 | 8/2003 | Grosshans et al. |
| 2004/0169137 A1 | 9/2004 | Westphall et al. |
| 2005/0236375 A1 | 10/2005 | Gefter et al. |
| 2007/0254352 A1 | 11/2007 | Schaffer et al. |
| 2009/0020694 A1 | 1/2009 | Flory |
| 2009/0078866 A1 | 3/2009 | Li et al. |
| 2010/0084549 A1 | 4/2010 | Ermakov et al. |
| 2010/0084552 A1 | 4/2010 | Kawana |
| 2010/0090102 A1 | 4/2010 | Rather et al. |
| 2010/0227310 A1 | 9/2010 | Manalis et al. |
| 2010/0234837 A1 | 9/2010 | Alfano |
| 2010/0314538 A1 | 12/2010 | Makarov et al. |
| 2010/0320377 A1 | 12/2010 | Cotter |
| 2011/0095175 A1 | 4/2011 | Bateman |
| 2011/0240845 A1 | 10/2011 | Ding |
| 2012/0112056 A1 | 5/2012 | Brucker et al. |
| 2012/0282641 A1 | 11/2012 | Reilly et al. |
| 2013/0175440 A1 | 7/2013 | Perelman et al. |
| 2013/0124099 A1 | 8/2013 | Ecker |
| 2013/0200261 A1 | 8/2013 | Mizutani et al. |
| 2013/0234017 A1 | 9/2013 | Kaltashov et al. |
| 2013/0327934 A1 | 12/2013 | Makarov et al. |
| 2014/0197333 A1 | 7/2014 | Joliffe et al. |
| 2014/0346344 A1 | 11/2014 | Chen |
| 2015/0008316 A1 | 1/2015 | Guna |
| 2015/0021472 A1 | 1/2015 | Makarov |
| 2015/0325425 A1 | 11/2015 | Makarov |
| 2015/0331000 A1* | 11/2015 | Collier ............ C07K 14/775 506/18 |
| 2016/0005580 A1 | 1/2016 | Grinfeld |
| 2016/0035556 A1 | 2/2016 | Berkout et al. |
| 2016/0181084 A1 | 6/2016 | Smith |
| 2016/0336165 A1 | 11/2016 | Guna |
| 2017/0040152 A1 | 2/2017 | Makarov |
| 2017/0307565 A1 | 10/2017 | Clemmer et al. |
| 2017/0372883 A1 | 12/2017 | Verenchikov |
| 2020/0243317 A1 | 7/2020 | Lopez-Hilfiker et al. |

FOREIGN PATENT DOCUMENTS

| | | | |
|---|---|---|---|
| WO | 2000028004 A1 | 5/2000 | |
| WO | 2000028061 A1 | 5/2000 | |
| WO | 2001092551 A2 | 5/2001 | |
| WO | 2003042704 A1 | 5/2003 | |
| WO | WO-03042704 A1 * | 5/2003 | ......... G01N 15/0266 |
| WO | 2006130474 A2 | 12/2006 | |
| WO | 2010135830 A1 | 12/2010 | |
| WO | 20120083031 A1 | 6/2012 | |
| WO | 2012145037 A1 | 10/2012 | |
| WO | 016073850 A1 | 5/2016 | |
| WO | 017162779 A1 | 9/2017 | |
| WO | 20170190031 A1 | 11/2017 | |
| WO | 20190140233 | 7/2019 | |
| WO | 2019231854 A1 | 12/2019 | |

OTHER PUBLICATIONS

Hutchins et al., "Accurate Quantification of High Density Lipoprotein Particle Concentration by Calibrated Ion Mobility Analysis" Clin Chem. 60(11): 1393 (Nov. 2014) (Year: 2014).*

Heller et al. "Mass spectrometry-based analytical tools for the molecular protein characterization of human plasma lipoproteins" 5 Proteomics 2619 (2005) (Year: 2005).*

Karathanasis et al., The Changing Face of HDL and the Best Way to Measure It, 63 Clinical Chemistry 196 (2017) (Year: 2017).*

Heller et al, "Mass Spectrometry-Based Analytical Tools For the Molecular Protein Characterization of Human Plasma Lipoproteins", Proteomics, 2005, 5, 2619-2630 (Year: 2005).*

PCT International Search Report and Written Opinion completed Dec. 12, 2019 and issued in connection with PCT/US2018/051944.

David Z. Keifer et al, "Charge detection mass spectrometry: weighing heavier things", The Analyst, vol. 142, No. 10, Jan. 1, 2017 (Jan. 1, 2017), p. 1654-1671.

Manfred Heller et al, "Mass spectrometry-based analytical tools for the molecular protein characterization of human plasma lipoproteins", Proteomics, vol. 5, No. 10, Jul. 1, 2005 (Jul. 1, 2005), p. 2619-2630.

Draper, Benjamin E., "The FUNPET—a New Hybrid Ion Funnel-Ion Carpet Atmospheric Pressure Interface for the Simultaneous Transmission of a Broad Mass Range", Journal of the American Society of Mass Spectrometry 29, 2160-2172, Aug. 15, 2018.

El-Baba, Tarick J., et al., "Melting Proteins Confined in Nanodroplets With 10.6 um Light Provided Clues About Early Steps of Denaturation", Chemical Communications, vol. 54, No. 26, 3270-3273, 2018.

Ukreja, Alexander A., et al. "Structurally Similar Woodchuck and Human Hepadnavirus Core Proteins Having Distinctly Different Temperature Dependencies of Assembly" Journal of Virology, vol. 68, No. 24, 14105-14115, Sep. 24, 2014.

PCT International Search Report and Written Opinion completed by the ISA/EP on Sep. 9, 2019 and issued in connection with PCT/US2019/035379.

PCT International Search Report and Written Opinion completed by the ISA/EP on Aug. 27, 2019 and issued in connection with PCT/US2019/035381.

PCT International Search Report and Written Opinion completed by the ISA/EP on Mar. 8, 2021 and issued in connection with PCT/US2020/065300.

PCT International Search Report and Written Opinion completed by the ISA/EP on Mar. 8, 2021 and issued in connection with PCT/US2020/065301.

PCT International Search Report and Written Opinion completed by the ISA/US on Apr. 5, 2021 and issued in connection with PCT/US2021/016435.

PCT International Search Report and Written Opinion completed by the ISA/US on Mar. 18, 2021 and issued in connection with PCT/US2021/016325.

Charge Detection Mass Spectrometry of Bacteriophage P22 Procapsid Distributions Above 20MDa, David Keifer et al, Rapid Communications in Mass Spectrometry, vol. 28, No. 5.

(56) References Cited

OTHER PUBLICATIONS

Charge Detection Mass Spectrometry: Instrumentation & Applications to Viruses, Elizabeth Pierson, Proquest Dissertations and Theses; Thesis (Ph.D.) vol. 76-09(E), Section: B. 168.
Defining the Stoichiometry and Cargo Load of Viral and Bacterial Nanoparticles by Orbitrap Mass Spectrometry, Snijder, J. et al, J. Am. Chem. Soc. 2014, 136, 7295-7299.
Analysis of a Common Cold Virus and Its Subviral Particles by Gas-Phase Electrophoretic Mobility Molecular Analysis and Native Mass Spectrometry, Weiss Vu et al, Anal Chem. 2015.
Product-Related Impurities in Clinical-Grade Recombinant AAV Vectors: Characterization and Risk Assessment, J Fraser Wright, Biomedicines 2014, 2, 80-97.
European Office Action dated Sep. 2, 2021 in application 19 707 901.5.
Koizumi et al., A novel phase-coherent programmable clock for high-precision arbitrary waveform generation applied to digital ion trap mass spectrometry_ Int. J_ Mass Spectrom_ 292, 23-31 (2010).
Konenkov et al., Matrix methods for the calculation of stability diagrams in quadrupole mass spectrometry. J. Amer. Soc. Mass Spec. 13, 597-613 {2002).
Landais et al., Varying the radio frequency: A new scanning mode for quadrupole analyzers. Rapid Commun. Mass Spectrom. 12, 302-306 (1998).
Makarov, Alexander, "Electrostatic Axially Harmonic Orbital Trapping: A High-Performance Technique of Mass Analysis", Analytical Chemistry, vol. 72, No. 6, Mar. 1, 2000 (Mar. 1, 2000), p. 1156-1162.
Marmei et al., A frequency-swept quadrupole mass filler. Int. J_ Mass Spectrom. Ion Proc. 42, 3-10 (1982).
Martin, Stability of doubly charged alkali halide clusters. J_ Chem. Phys. 76, 5467-5469 (1982).
Miyamura, K., et al. "Parvovirus Particles as Platforms for Protein Presentation", National Academy of Sciences, vol. 1, No. 18,pp. 8507-8511 (Aug. 30, 1994).
Mori, Seiichiro, Mori, et al. "Two novel adeno-associated viruses from cynomolgus monkey: pseudotyping characterization of capsid protein", Virology 330, pp. 375-383 (2004).
Muzyczka, N., "Use of Adeno-Associated Virus as a General Transduction Vector for Mammalian Cells", Current Topics n Microbiology and Immunology, vol. 158, pp. 97-129 (1992).
Muramatsu, S., et al. "Nucleotide Sequencing and Generation of an Infectious Clone of Adeno-Associated Virus 3", Virology vol. 221; Article No. 0367; pp. 208-217 (1996).
Padron, Eric, et al. "Structure of Adeno-Associated Virus Type 4", Journal of Virology, vol. 79, No. 8, pp. 5047-5058 Apr. 2005).
Puttaraju, M., et al. "Spliceosome-mediated RNA trans-splicing as a tool for gene therapy", Nature Biotechnology, vol. 17, pp. 246-252 (Mar. 1999).
Nie et al., Frequency scan of a quadrupole mass analyzer in the third stability region for protein analysis. J. Chin. Chem_ Soc , 53, 47-52 (2006).
Paul et al., Das elektrische massenfilter als massenspektromeler und isotopenlrenner. Z. Phys. 152, 143-182 (1958).
Paul, et al., Das elektrische massenfiller, Z. Phys. 140, 262-273 (1955).
Pierson, Elizabeth E., et al., "Detection of 1-15 Late Intermediates in Virus Capsid Assembly by Charge Detection Mass Spectrometry", Journal of the American Chemical Society, vol. 136, No. 9, Feb. 19, 2014, 3536-3541.
Pierson, Elizabeth E., et al., Charge Detection Mass Spectrometry for Single Ions with an Uncertainty in the Charge Measurement of 0.65 e; Elizabeth E_ Pierson et al.; Journal American Society for Mass Spectrometry, vol. 26, pp. 1213-1220 (2015).
Pierson, Elizabeth E., et al. "Charge Detection Mass Spectrometry Identifies Preferred Non-icosahedral Polymorphs in the Self-Assembly of Woodchuck Hepatitis Virus Capsids", Jour. of Molecular Biology, vol. 428, Issue 2, pp. 292-300. Jan. 29, 2016.

Schlunegger et al., Frequency scan for the analysis of high mass ions generated by matrix-assisted laser esorption/ionization in a Paul trap_ Rapid Commun. Mass Spectrom. 13, 1792-1796 (1999).
Richards et al., A new operating mode for the quadrupole mass filler. Int. J. Mass Spectrom. Ion Phys. 12, 317-339 1973).
Richards et al., Waveform parameter tolerances for the quadrupole mass filler with rectangular excitation. Int. J. Mass Spectrom. Ion Phys_ 15, 417-428 (1974).
Sonalikar, Hrishikesh S., et al. "Numerical analysis of segmented-electrode Orbitraps", International Journal of Mass Spectrometry, Elsevier Science Publishers, Amsterdam, NL, vol. 395, Dec. 17, 2015 (Dec. 17, 2015), p. 36-48.
Shinholt, Review of Scientific Instruments. 85, 113109 (2014); doi: 10.1063/1.4900627.
Sobott et al., A tandem mass spectrometer for improved transmission and analysis of large macromolecular Assemblies. Anal. Chem. 74, 1402-1407 (2002).
Syed, et al., Quadrupole mass filler: Design and performance for operation in stability zone 3. J. Am. Soc. Mass Spectrom. 24, 1493-1500 (2013).
Shade, Rosemary, et al. "Nucleotide Sequence and Genome Organization of Human Parvovirus B19 Isolated from the Serum of a Child during plastic Crisis", Journal of Virology, vol. 58, No. 3, pp. 921-936 {Jun. 1986).
Sharp, Phillip A., et al. "RNA Interference", American Association for the Advancement of Science; Science, New Series, vol. 287, No. 5462, pp. 2431-2433 {Mar. 31, 2000).
Shi, Z., et al. "Insertional Mutagenesis at Positions 520 and 584 of Adena-Associated Virus Type 2 (MV2) Capsid Gene and Generation of MV2 Vectors with Eliminated Heparin-Binding Ability and Introduced Novel Tropism", Human Gene Therapy, vol. 17, pp. 353-361 (Mar. 2006).
Srivastava, Arun, et al., "Nucleotide Sequence and Organization of the Adena-Associated Virus 2 Genome", Journal of Virology, vol. 45, No. 2, pp. 555-564 {Feb. 1983).
Tsao, Jun, et al., "The Three-Dimensional Structure of Canine Parvovirus and Its Functional Implications", American Association for the Advancement of Science, Science, New Series, vol. 251, No. 5000, pp. 1456-1464 {Mar. 22, 991).
Walters, Robert W., "Structure of Adeno-Associated Virus Serotype 5", Journal of Virology, vol. 78, No. 7, pp. B361-3371 {Apr. 2004).
Wang, Lei, et al., "Expanding the Genetic Code", Annual Review of Biophysics and Biomolecular Structure, vol. 35, pp. 25-249 {2006).
Xie, Qing, et al., "Canine Parvovirus Capsid Structure, Analyzed at 2.9 A Resolution", Journal of Molecular Biology, vol. 64, pp. 497-520 (1996).
Xie, Qing, et al., "The atomic structure of adeno-associated virus (MV-2), a vector for human gene therapy", PNAS, vol. 99, No. 16, pp. 10405-10410 (Aug. 6, 2002).
Xiao, Weidong, et al., "Gene Therapy Vectors Based on Adena-Associated Virus Type 1", Journal of Virology, vol. 73, No. 5, pp. 3994-4003 (May 1999).
Uetrecht et al., "Stability and Shape of Hepatitis B Virus Capsids In Vacuo", Angew. Chem. Int. Ed. 2008, 47, 6247-6251.
Uetrecht et al., "High-resolution mass spectrometry of viral assemblies: Molecular composition and stability of dimorphic hepatitis B virus capsids", PNAS 2008, vol. 105, 9216-9920.
Winger et al., Observation and implications of high mass-lo-charge ratio ions from electrospray ionization mass spectrometry, J_ Am_ Soc_ Mass Spectrom. 4, 536-545 (1993).
Xiong, et al., The development of charge detection-quadrupole ion trap mass spectrometry driven by rectangular and triangularwaves, Analyst 137, 1199-1204 (2012).
Yang, et al., Development of a palm portable mass spectrometer. J. Amer. Soc. Mass Spec. 19, 1442-1448 (2008).
Yost, et al., Selected ion fragmentation with a tandem quadrupole mass spectrometer. J. Am. Chem. Soc. 100, 274-2275 (1978).
Bioconjugate Techniques; Hermanson; .Academic Press, 1st Edition (1996),. (book reference, chapter guide attached; book/specific chapter(s) to be made available upon request).
Botamanenko, Daniel, et al., "Ion-Ion Interactions in Charge Detection Mass Spectrometry", J Am Soc Mass Spectrom. Dec. 2019 ; 30(12): 2741-2749 doi:10.1007/s13361-019-02343-y.

(56) References Cited

OTHER PUBLICATIONS

Draper, Benjamin E., et al., "Real-Time Analysis and Signal Optimization for Charge Detection Mass Spectrometry", J. Am. Soc. Mass Spectrom. (2019) 30:898Y904.

Todd, Aaron R., et al. "Implementation of a Charge-Sensitive Amplifier without a Feedback Resistor for Charge Detection Mass Spectrometry Reduces Noise and Enables Detection of Individual Ions Carrying a Single Charge", J. Am. Soc. Mass Spectrom. 2020, 31, 146-154.

PCT International Search Report and Written Opinion completed by the ISA/EP on Jul. 14, 2020 and issued in connection with PCT/US2020/029287.

PCT International Search Report and Written Opinion completed by the ISA/US on Nov. 23, 2020 and issued in connection with PCT/US2020/052009.

PCT International Search Report and Written Opinion completed by the ISA/US on Jan. 24, 2021 and issued in connection with PCT/US2020/054975.

PCT International Search Report and Written Opinion completed by the ISA/EP on Apr. 18, 2019 and issued in connection with PCT/US2019/013251.

PCT International Search Report and Written Opinion completed by the ISA/EP on Apr. 16, 2019 and issued in connection with PCT/US2019/013274.

PCT International Search Report and Written Opinion completed by the ISA/EP on Mar. 27, 2019 and issued in connection with PCT/US2019/013277.

PCT International Search Report and Written Opinion completed by the ISA/EP on Jul. 24, 2019 and issued in connection with PCT/US2019/013278.

PCT International Search Report and Written Opinion completed by the ISA/EP on Sep. 9, 2019 and issued in connection with PCT/US2019/013279.

PCT International Search Report and Written Opinion completed by the ISA/EP on Mar. 28, 2019 and issued in connection with PCT/US2019/013280.

PCT International Search Report and Written Opinion completed by the ISA/EP on Aug. 27, 2019 and issued in connection with PCT/US2019/013281.

PCT International Search Report and Written Opinion completed by the ISA/EP on Mar. 27, 2019 and issued in connection with PCT/US2019/013283.

PCT International Search Report and Written Opinion completed by the ISA/EP on Mar. 29, 2019 and issued in connection with PCT/US2019/013284.

PCT International Search Report and Written Opinion completed by the ISA/EP on Jul. 26, 2019 and issued in connection with PCT/US2019/013285.

PCT International Search Report and Written Opinion completed by the ISA/US on Jan. 12, 2016 and issued in connection with PCT/US2015/059463.

PCT International Search Report and Written Opinion completed by the ISA/US on Jun. 19, 2017 and issued in connection with PCT/US2017/030163.

Supplemental European Search Report for European Patent Application No. 17790559.3 dated Nov. 12, 2019 (11 pages).

Anthony, Staci N. "MS /MS instrumentation for megadalton-sized ions", 2016, XP055619426, ISBN: 978-1-369-02558-3 Retrieved from the Internet: URL:https://search.proquest.com/docview/1830450391?accountid=29404.

Anthony, et al., A simple electrospray interface based on a DC ion carpet, Int. J. Mass Spectrom. 371, 1-7 (2014).

Bantel-Schall, U., et al., "Human Adena-Associated Virus Type 5 Is Only Distantly Related to Other Known Primate Helper-Dependent Parvoviruses", Journal of Virology, vol. 73, pp. 939-947 {Feb. 1999).

Beuhler, et al., Threshold studies of secondary electron emission induced by macro ion impact on solid surfaces. Nucl. Instrum. Methods. 170, 309-315 (1980).

Beuhler, et al., A study of the formation of high molecular weight water cluster ions {m/e<59000) in expansion of ionized gas mixtures, J. Chem. Phys. 77, 2549-2557 (1982).

Brancia, et al., Digital asymmetric waveform isolation {DAWI) in a digital linear ion trap. J_ Am. Soc_ Mass Spectrom. 1. 1530-1533 (2010).

Brown, C., et al. "Chimeric Parvovirus B19 Capsids for the Presentation of Foreign Epitope",; Virology 198, pp. J77-488 (1994).

Burnham, et al. "Analytical Ultracentrifugation as an Approach to Characterize Recombinant Adena-Associated Viral Vectors", Human Gene Therapy Methods, vol. 26, No. 6; pp. 228-242, Oct. 15, 2015.

Chao, Hengjun, et al. "Several Log Increase in Therapeutic Transgene Delivery by Distinct Adena-Associated Viral Serotype Vectors" Molecular Therapy vol. 2, No. 6, pp. 619-623 {Dec. 2000).

Chiorini, John A., et al. "Cloning of Adeno-Associated Virus Type 4 (MV4) and Generation of Recombinant MV4 Particles",Journal of Virology, vol. 71, pp. 6823-6833 {Sep. 1997).

Chiorini, John A., "Cloning and Characterization of Adeno-Associated Virus Type 5", Journal of Virology, vol. 73, DP-1309-1319 {Feb. 1999).

Chernushevich, et al., Collisional cooling of large ions in electrospray mass spectrometry. Anal. Chem 76. H54-1760 (2004).

Cleves, Ann E., "Protein transport: The nonclassical ins and outs", Current Biology, vol. 7, No. 5, pp. 318-320 (1997).

Contino, Nathan Colby, "Ion trap charge detection mass spectrometry: Lowering limits of detection and improving signal to noise", ISBN: 9781303535048, Jul. 30, 2013 (Jul. 30, 2013).

Ding, et al., A simulation study of the digital ion trap mass spectrometer. Int. J. Mass Spectrom. 221, 117-138 {2002).

Ding, et al, A digital ion trap mass spectrometer coupled with atmospheric pressure ion sources. J_ Mass Spectrom. 69, 471-484 (2004).

Douglas J_ Linear quadrupoles in mass spectrometry. Mass Spectrom. Rev. 28, 937-960 (2009).

Doussineau, Tristan, et al. "Infrared multiphoton dissociation tandem charge detection-mass spectrometry of single megadalton electrosprayed ions", Review of Scientific Instruments, AIP, Melville, NY, US, vol. 82, No. 8, Aug. 1, 2011, pp. 84104-84104.

Elliott, Andrew G., et al. "Simultaneous Measurements of Mass and Collisional Cross-Section of Single Ions with charge Detection Mass Spectrometry", Analytical Chemistry, vol. 89, No. 14, Jun. 16, 2017, pp. 7701-7708.

Elliott, Andrew G., et al. "Effects of Individual Ion Energies on Charge Measurements in Fourier Transform Charge Detection Mass Spectrometry (FT-CDMS)", Journal of the American Society for Mass Spectrometry., Nov. 14, 2018 (Nov. 14, 2018).

Elliott, Andrew G., et al. "Single Particle Analyzer of Mass: A Charge Detection Mass Spectrometer with a Multi-Detector Electrostatic Ion Trap", International Journal of Mass Spectrometry, Elsevier Science Publishers, Amsterdam, NL, vol. 414, Jan. 15, 2017, pp. 45-55.

Emerson, S., et al. "Hepatitis E Virus", Virology, vol. 2, Chapter 70; (4th ed., Lippincott-Raven Publishers).

Fields, Bernard, et al. "Darvoviridae: The Viruses and Their Replication" Virology, vol. 2, Chapter 69, pp. 2327-2359; 4th ed., Lippincott-Raven Publishers).

Fuerstenau, et al., "Mass Spectrometry of an Intact Virus", Agnew. Chem. 2001, 559-562.

Gao, Guangping, et al. "Clades of Adeno-Associated Viruses Are Widely Disseminated in Human Tissues", vol. 78, pp. 6381-6388 (Jun. 2004).

Gao, Guangping, et al. "Novel Adeno-Associated Viruses from Rhesus Monkeys as Vectors for Human GeneTherap",.; National Academy of Sciences, vol. 99, No. 18, pp. 11854-11859 {Sep. 3, 2002).

Gorman, Linda, et al. "Stable Alteration of Pre-mRNA Splicing Patterns by Modified U7 Small Nuclear RNAs", National Academy of Sciences, vol. 95, No. 9, pp. 4929-4934 (Apr. 28, 1998).

Grifman, M., et al. "Incorporation of Tumor-Targeting Peptides into Recombinant Adeno-associated Virus Capsids",.; Molecular Therapy, vol. 3, No. 6, pp. 964-975 (Jun. 2001).

(56) References Cited

OTHER PUBLICATIONS

Grinfeld, Dmitry, et al. "Space-Charge Effects in An Electrostatic Multireflection Ion Trap", European Journal of Mass Spectrometry, vol. 20, No. 2, Apr. 1, 2014 (Apr. 1, 2014), p. 131-142.

Hauck, B., et al. "Characterization of Tissue Tropism Determinants of Adeno-Associated Virus Type 1", Journal of Virology, vol. 77, No. 4, pp. 2768-2774 (Feb. 2003).

Hogan, Joanna, et al. "Optimized Electrostatic Linear Ion Trap for Charge Detection Mass Spectrometry", Jul. 9, 2018 (Jul. 9, 2018), vol. 29, No. 10, p. 2086-2095.

Keifer, David Z., "Single-Molecule Mass Spectrometry", Mass Spectrometry Reviews, vol. 36 pp. 715-733 (2017).

Keifer, David Z., et al. "Charge Detection Mass Spectrometry with Almost Perfect Charge Accuracy", Analytical Chemistry, vol. 87, No. 20, Oct. 20, 2015, pp. 10330-10337.

Kelly, Ryan T., et al. "The ion funnel: Theory, implementations, and applications", Mass Spectrometry Reviews., vol. 29, Apr. 23, 2009, pp. 294-312.

Kim et al., A multicapillary inlet jet disruption electrodynamic ion funnel interface for improved sensitivity using tmospheric pressure ion sources. Anal. Chem. 73, 4162-4170 {2001).

Examination Report issued by EP Patent Office dated Nov. 15, 2022 in EP application 18819225.6.

PCT International Search Report and Written Opinion completed by the ISA/US on Oct. 11, 2021 and issued in connection with PCT/US2021/034480.

Fernandez-Maestre et al. "Ammonia as a Modifier in Ion Mobility Spectrometry: Effects on Ion Mobilities and Potential as a Separation Tool", J. Chil. Chem. Soc. 2014. 59, No. 1, especially; abstract; p. 2398, col. 1, para 1; p. 2398, col. 1, para 2; p. 2398, col. 2, para 2; p. 2399, Figure 1; p. 2402, col. 1, para 1; p. 2402, col. 2, para 1; Figure 6a. Figure 6b.

Kafle et al. "Understanding gas phase modifier interactions in rapid analysis by Differential Mobility-Tandem Mass Spectrometry", J Am Soc Mass Spectrom. 2014. 25(7): pp. 1098-1113, especially: p. 7, para 2; p. 10, para 5; p. 11, para 1.

Kiss et al. "Size, weight and position: ion mobility spectrometry and imaging MS combined", Anal Bioanal Chem. 2011. 399: pp. 2623-2634, especially: p. 2626, col. 1, para 1.

* cited by examiner

METHODS FOR RESOLVING LIPOPROTEINS WITH MASS SPECTROMETRY

CROSS-REFERENCE TO RELATED APPLICATION

This is a national stage entry of International Patent Application No. PCT/US2018/051944, filed Sep. 20, 2018, which claims the benefit of and priority to U.S. Provisional Patent Application No. 62/561,184, filed Sep. 20, 2017, the disclosures of which are expressly incorporated herein by reference in their entireties.

STATEMENT OF GOVERNMENT RIGHTS

This invention was made with government support under CHE1531823 awarded by National Science Foundation. The government has certain rights in the invention.

BACKGROUND

Lipoproteins are involved in cholesterol transport in human plasma, have a diverse range of metabolic function, and serve as biomarkers for coronary artery disease. Lipoproteins are separated into classes based on the density of protein relative to the lipid composition, including high-density (HDL), low-density (LDL), and very low-density (VLDL). HDL is commonly referred to as the "good cholesterol," while high amounts of LDL, or "bad cholesterol" have been implicated in coronary artery disease. There is an inverse correlation of HDL particle concentration and cardiovascular disease. (Castelli, W. P., et al. *Circulation.* 1977 (55) 767-772, incorporated by reference herein).

Each density class can be split into several subtypes which differ in size, composition, and metabolic properties. Furthermore, each subtype contains particles that differ in number of structural proteins, giving rise to many possible protein/lipid combinations that encompass a range of unique structures. The major density classes are linked through a series of lipid and protein exchange and conversion during metabolism, causing great variation in particle mass for a single population. Information about the many subtypes and diverse subpopulations of HDL is currently incomplete (Karathanasis, S. K., et al. *Clin. Chem.* 2017 (63) 196-210, incorporated by reference herein).

Characterizing macromolecular complexes is challenging because the resolution of conventional mass analyzers is not sufficient to assign charge states in the mass-to-charge (m/z) spectrum for heterogeneous and highly charged complexes, such as lipoproteins. Peaks in the m/z spectrum broaden and shift due to mass heterogeneity, either intrinsic or due to complex formation. Poorly resolved peaks in the m/z spectrum prevent charge state assignment and mass determination. Even sub-megadalton (MDa) sized complexes can contain hundreds of charges, making it a challenge to accurately determine mass.

While the development of new therapies for improved cardiovascular health would benefit from the development of techniques to measure HDL and LDL subtypes directly, particle diversity and heterogeneity impede characterization by analytical techniques known in the art. Thus, there is a need for new methods for analyzing lipoproteins.

SUMMARY

The present disclosure provides methods for resolving lipoproteins using single particle mass spectrometry, such as charge detection mass spectrometry (CDMS). Distinct subpopulations that exist within lipoprotein classes are revealed by correlating m/z and mass (or by other correlations involving mass, charge and m/z measurements).

According to one aspect of the present disclosure, a method of identifying components present in a lipoprotein includes subjecting the lipoprotein to mass spectrometry to produce ions, measuring a charge of each ion, measuring a mass-to-charge ratio of the ion, and identifying the components based on the mass of the lipoprotein.

In some embodiments, the charge of the ion and the mass-to-charge ratio of the ion may be measured simultaneously. In some embodiments, the charge of the ion and the mass-to-charge ratio of the ion may be measured using charge detection mass spectrometry. In some embodiments, the charge detection mass spectrometry may include focusing the ion into a linear ion trap, the linear ion trap comprising a charge detection cylinder. In some embodiments, the charge detection mass spectrometry may include focusing the ion into a linear ion trap and the linear ion trap incorporates a charge detection cylinder. In some embodiments, the linear ion trap may be a cone trap.

In some embodiments, the mass-to-charge ratio of the ion may be measured based on a time period that the ion takes to traverse the charge detection cylinder or the fundamental frequency at which the ion oscillates in the charge detection cylinder.

In some embodiments, the charge of the ion may be measured based on the amplitude of a signal due to the ion oscillating in the charge detection cylinder. In some embodiments, the ion may be trapped in the linear ion trap for a trapping period to determine the mass to charge ratio of the ion with sufficient accuracy. For example, the ion may be trapped in the linear ion trap for a trapping period of about 50 ms to about 150 ms.

In some embodiments, the lipoprotein may include one or more of high-density lipoprotein particles (HDL), low-density lipoprotein particles (LDL), and very low density lipoprotein particles (VLDL). In some embodiments, the method may further include estimating the diameter of a particle of the lipoprotein based on the mass of the ion and the density of a known lipoprotein subtype particle. In some embodiments, the lipoprotein may include a plasma lipoprotein, and the ion may be in the presence of one or more other lipoprotein particles.

In some embodiments, the mass of the ion may be within about 1 MDa of one or more other lipoprotein particles having a different subtype compared to the ion. In other embodiments, the mass of the ion may be within about 100 kDa of one or more other lipoprotein particles having a different subtype compared to the ion. Yet, in some embodiments, the mass of the ion may be within about 20 kDa of one or more other lipoprotein particles having a different subtype compared to the ion. In some embodiments, the ion may be an intact lipoprotein particle. In some embodiments, subjecting the lipoprotein to mass spectrometry to produce ions may include subjecting the lipoprotein without isolating a lipoprotein particle prior to subjecting the lipoprotein to mass spectrometry to produce an ion.

In some embodiments, the mass of the ion may be from about 100 kDa to about 80 MDa. In some embodiments, the mass of the ion may be from about 10 MDa to about 80 MDa. In some embodiments, the mass of the ion may be from about 100 kDa to about 3 MDa. In some embodiments, the method may include subjecting a single sample to a mass spectrometer.

According to another aspect of the present disclosure, a method for evaluating a patient's risk of cardiovascular disease includes identifying components present in a lipoprotein according to any of the preceding clauses. In some embodiments, identifying components present in a lipoprotein may include identifying components present in a lipoprotein in a blood sample.

According to another aspect of the present disclosure, a method of identifying components present in a lipoprotein includes correlating m/z and charge, or quantities derived therefrom, to determine quantities of HDL, LDL, and VLDL, wherein the lipoprotein is part of a sample comprising serum.

According to another aspect of the present disclosure, a method of identifying components present in a lipoprotein includes correlating m/z and charge, or quantities derived therefrom, to determine subtypes of HDL, LDL, and VLDL, wherein the lipoprotein is part of a sample comprising whole blood.

According to another aspect of the present disclosure, a method of identifying components of a lipoprotein present in a sample includes subjecting the sample to mass spectrometry to produce ions, measuring a charge of each ion, measuring a mass-to-charge ratio of the ion, and identifying the components based on the mass of the sample.

In some embodiments, the sample may include at least one of whole blood, plasma, or serum. In some embodiments, the charge of the ion and the mass-to-charge ratio of the ion may be measured simultaneously. In some embodiments, the charge of the ion and the mass-to-charge ratio of the ion may be measured using charge detection mass spectrometry. In some embodiments, the charge detection mass spectrometry may include focusing the ion into a linear ion trap, the linear ion trap comprising a charge detection cylinder. In some embodiments, the charge detection mass spectrometry may include focusing the ion into a linear ion trap and the linear ion trap incorporates a charge detection cylinder. In some embodiments, the linear ion trap may be a cone trap. In some embodiments, the mass-to-charge ratio of the ion may be measured based on a time period that the ion takes to traverse the charge detection cylinder or the fundamental frequency at which the ion oscillates in the charge detection cylinder.

In some embodiments, the charge of the ion may be measured based on the amplitude of a signal due to the ion oscillating in the charge detection cylinder. In some embodiments, the ion may be trapped in the linear ion trap for a trapping period to determine the mass to charge ratio of the ion with sufficient accuracy. In some embodiments, the ion may be trapped in the linear ion trap for a trapping period of about 50 ms to about 150 ms. In some embodiments, the lipoprotein may include one or more of high-density lipoprotein particles (HDL), low-density lipoprotein particles (LDL), and very low density lipoprotein particles (VLDL).

According to another aspect of the present disclosure, a method of identifying components present in a lipoprotein including subjecting the sample to mass spectrometry to produce ions, separating the ions based on a mass-to-charge ratio, selecting a subset of the ions based on the mass-to-charge ratio, dissociating the selected ions into fragments, and analyzing the fragments to identify the components present in the lipoprotein.

In some embodiments, selecting the subset of the ions based on the mass-to-charge ratio may include selecting a subset of the ions that correspond to a subpopulation of the lipoprotein based on the mass-to-charge ratio. For example, the mass-to-charge ratio may correspond to a subpopulation of the lipoprotein.

In some embodiments, selecting the subset of the ions based on the mass-to-charge ratio may include selecting a subset of the ions using a mass spectrometer. For example, the mass spectrometer may be a time-of-flight mass spectrometer, a quadrupole mass spectrometer, a linear and non-linear ion trap mass spectrometer, a Fourier transform mass spectrometer, a magnetic sector mass spectrometer, an Orbitrap mass spectrometer, or a double focusing mass spectrometer.

In some embodiments, dissociating the selected ions into the fragments may include dissociating the selected ions using a dissociation method. For example, the dissociation method may be collision induced dissociation, collisionally activated dissociation, surface induced dissociation, photo-induced dissociation, electron-impact induced dissociation, electron transfer dissociation, and/or electron capture dissociation. The photo-induced dissociation may further include infrared multiple photon dissociation and/or UV photodissociaton.

In some embodiments, analyzing the fragments to identify the components present in the lipoprotein may include analyzing the fragments using mass spectrometry and/or charge detection mass spectrometry. In some embodiments, the lipoprotein comprises one or more of high-density lipoprotein particles (HDL), low-density lipoprotein particles (LDL), and very low density lipoprotein particles (VLDL).

DETAILED DESCRIPTION

Figure 1A:
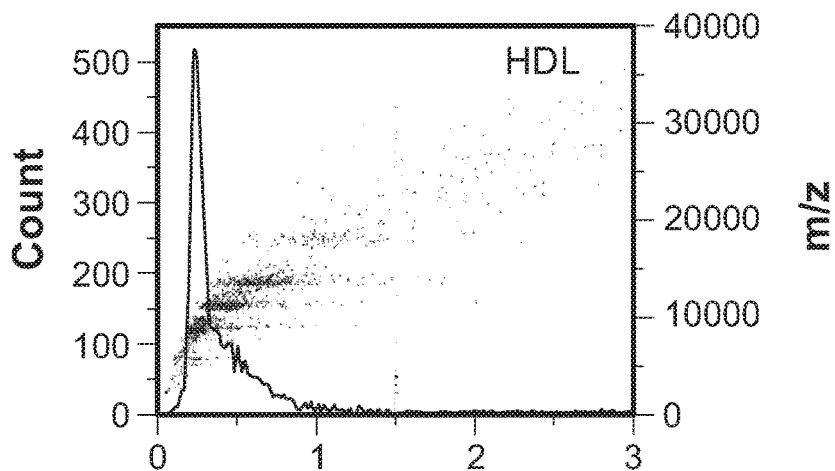
FIG. 1A is a mass spectrum for HDL overlaid with a scatter plot of m/z versus mass where each point represents a single ion.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference herein in their entirety.

The present disclosure provides methods for resolving lipoproteins by measuring the mass-to-charge ratio (m/z) and charge (z) of lipoprotein ions passing through a mass spectrometer. In some embodiments, these methods are used to characterize high-density (HDL) and low-density (LDL) lipoprotein particles, even when the particles are highly heterogeneous.

It is to be understood that lipoproteins may comprise micellar molecular structures having several structural proteins and lipid molecules. Lipoproteins may comprise tens of hundreds of lipid molecules.

HDL is comprised of approximately 50% protein by mass, of which, two major structural proteins apolipoprotein AI (Apo-AI) and apolipoprotein AII (Apo-AII), contribute to about 70% and about 20% of the total protein content, respectively. The additional 10% can be attributed to enzymes and lipid transfer proteins, as well as >5% corresponding to minor proteins. Lipid transfer proteins are mainly responsible for the exchange of lipids between lipoprotein particles, and thus, contribute to the unfixed masses of HDL particles. The primary contributor to heterogeneity of HDL is the conformational flexibility of the main structural protein Apo-AI. It dictates particle structure through scavenging phospholipids and thus driving the formation of small, medium, and large particles. As particle size increases, the number of Apo-AI proteins also increases; some HDL subtypes carry more than 4 Apo-AI molecules per particle. In addition, Apo-AI has the capacity to bind and interact with additional proteins where specific protein-protein complexes have been observed to form with HDL particles. Over 50 accessory proteins and more than 200 individual lipid species have been identified in human HDL structure and transport. Without having a fixed stoichiometry, combined with the dynamic nature of exchangeable proteins, it may be difficult to parse out a fixed mass for each subtype. In some embodiments, a range of masses and sizes may be used to broadly characterize the observed subpopulations within HDL and its subtypes.

The high density subtypes HDL-2 and HDL-3 can be separated further into five distinct subpopulations HDL2b, HDL2a, HDL3a, HDL3b, and HDL3c. Each subpopulation differs in size and protein composition, with the main differences between HDL-2 and HDL-3 subtypes corresponding to their lipid rich and lipid-poor construction, respectively.

Low density lipoproteins are greater in size than high density particles; the diameter of LDL is at least twice as large as HDL and incorporates hundreds more lipid molecules. The low density lipoprotein classes suffer from inherent heterogeneity due to the high ratio of lipids and cholesterol relative to protein. Larger VLDL is converted to LDL in the bloodstream through a series of delipidation steps. Structural protein apolipoprotein-B100 (apoB-100) is non-exchangeable and does not vary in terms of number of molecules per particle. Instead, there are several other ancillary proteins that comprise LDL that are dynamic and can be exchanged during cholesterol transport.

The methods of the present disclosure can be employed to establish the mass and stoichiometry of lipoprotein particles. In some embodiments, the methods described herein can be employed to distinguish between various lipoprotein particle subtypes. Subpopulations and subtypes that exist within lipoprotein classes may be identified by correlating m/z, charge, and mass to reveal distinct subpopulations that exist within lipoprotein classes and subtypes that would be difficult or impossible to observe by ensemble techniques alone. In some embodiments, the present methods are used to observe low abundant subpopulations that exist within subtypes of HDL. The methods of this disclosure can also be used to resolve differences in lipoprotein structure, morphology, orientation, size, chemical status, and the like. The lipoprotein particles used in connection with the present disclosure may comprise intact lipoprotein particles. Additionally, the lipoprotein particles may be analyzed without the use of isolation or without the use of extensive isolation.

It is to be understood that the masses of the lipoprotein particles used in connection with the present methods may range from about 100 kilodaltons (kDa) to about 10 megadaltons (MDa), about 100 kilodaltons (kDa) to about 5 megadaltons (MDa), about 100 kilodaltons (kDa) to about 3 megadaltons (MDa), or about 100 kilodaltons (kDa) to about 2 megadaltons (MDa), or about 10 megadalton (MDa) to about 80 megadaltons (MDa).

In some embodiments, many lipoprotein classes are present in a sample used in connection with the methods described herein. In some embodiments, the methods comprise subjecting a single sample to a mass spectrometer. In some embodiments, samples containing isolated subgroups are measured as standards to aid in characterizing particle properties such as stoichiometry.

Analytical methods described herein include single particle mass spectrometry, such as charge detection mass spectrometry (CDMS), which is a single particle technique that measures the mass-to-charge ratio (m/z) and charge (z) for each individual ion. Single particle mass spectrometry may allow for differentiating heterogeneous species in the mass spectrum by measuring, such as simultaneously measuring, m/z and z and directly deducing mass therefrom. Multiplying m/z and z gives the mass of a particle directly. In addition, the measured mass and known density information can be used to estimate the particle diameter. This information may be used for characterizing lipoprotein subtypes and subgroups that vary slightly in size and protein composition.

For example, single particle mass spectrometry methods described herein are capable of resolving HDL subtypes and subgroups within heterogeneous HDL samples by correlating the mass and m/z measurements (or by other correlations involving mass, charge and m/z measurements). The single particle measurement afforded by single particle mass spectrometry allows for low abundance populations to be observed. The ability to measure single particles one at a time allows for the measurement of low abundance species within the mixture of particles. Single particle mass spectrometry is also capable of providing the accurate mass of intact lipoprotein particles.

Nonlimiting examples of single particle mass spectrometry approaches that can be employed in the methods of this disclosure include time of flight mass spectrometry with a cryogenic detector, charge detection mass spectrometry (CDMS), quadrupole ion trap mass spectrometry with optical detection and charge detection, Fourier transform ion cyclotron resonance, Orbitrap mass spectrometry and micromechanical/nanomechanical oscillators. A detailed description of various single molecule mass spectrometry approaches included in this disclosure can be found in Keifer & Jarrold ("Single molecule mass spectrometry" Mass Spectrometry Reviews; DOI 10.1002/mas.21495 (2016) Wiley Periodicals, Inc.; the entire contents of which are incorporated by reference herein).

In some embodiments, information on lipoprotein subtypes is obtained by correlating m/z and mass (or by other correlations involving mass, charge and m/z measurements). This information may be obtained from the m/z spectrum alone if the results are calibrated by single particle mass spectrometry, such as CDMS. In such embodiments, a conventional mass spectrometer may be used to obtain information on subtypes once standards are calibrated, such as by CDMS.

In some embodiments, the methods described herein are used alongside additional techniques used to detect, quantify, and/or characterize lipoprotein composition. Additional techniques may comprise one or more of liquid chromatography, nuclear magnetic resonance, size exclusion chromatography, electrofiltration or two-dimensional electrophoretic mobility, and related proteomics approaches.

Charge detection mass spectrometry (CDMS) is a single particle technique, where the m/z and z of individual ions are measured concurrently, thereby allowing direct determination of the mass of each ion. Examples of CDMS are described in Keifer et al. (*Anal. Chem.*, 2015, 87 (20), pp 10330-10337) and Pierson et al. (*J. Am. Soc. Mass Spectrom.* (2015) 26:1213-1220), which are incorporated by reference herein. The methods described herein include using CDMS to analyze heterogeneous mixtures that are intractable by conventional MS methods.

Exemplary CDMS systems are described in Contino, N. C., et al., *Int. J. Mass Spectrom.* 2013, 345-347, 153-159; Contino, N. C.; et al., *J. Am. Soc. Mass Spectrom.* 2013, 24, 101-108; Pierson, E. E.; et al., *Int. J. Mass Spectrom.* 2013, 337, 50-56; Pierson, E. E.; et al., *J. Am. Soc. Mass Spectrom.* 2015, 26, 1213-1220; Keifer, D. Z.; et al., *Anal. Chem.* 2015, 87, 10330-10337, incorporated by reference herein. In some embodiments, CDMS comprises passing ions through a conductive cylinder. The charge induced by the ion when it is in the cylinder is detected by a charge sensitive preamplifier. The time the ion takes to traverse the length of the conductive tube is related to the m/z, while the amplitude of the induced charge imparted onto the cylinder can be used to determine z. In some embodiments, the detection cylinder is placed inside an ion trap so that an ion oscillates back and forth through the detection cylinder many times, improving the signal to noise ratio.

Figure 3:
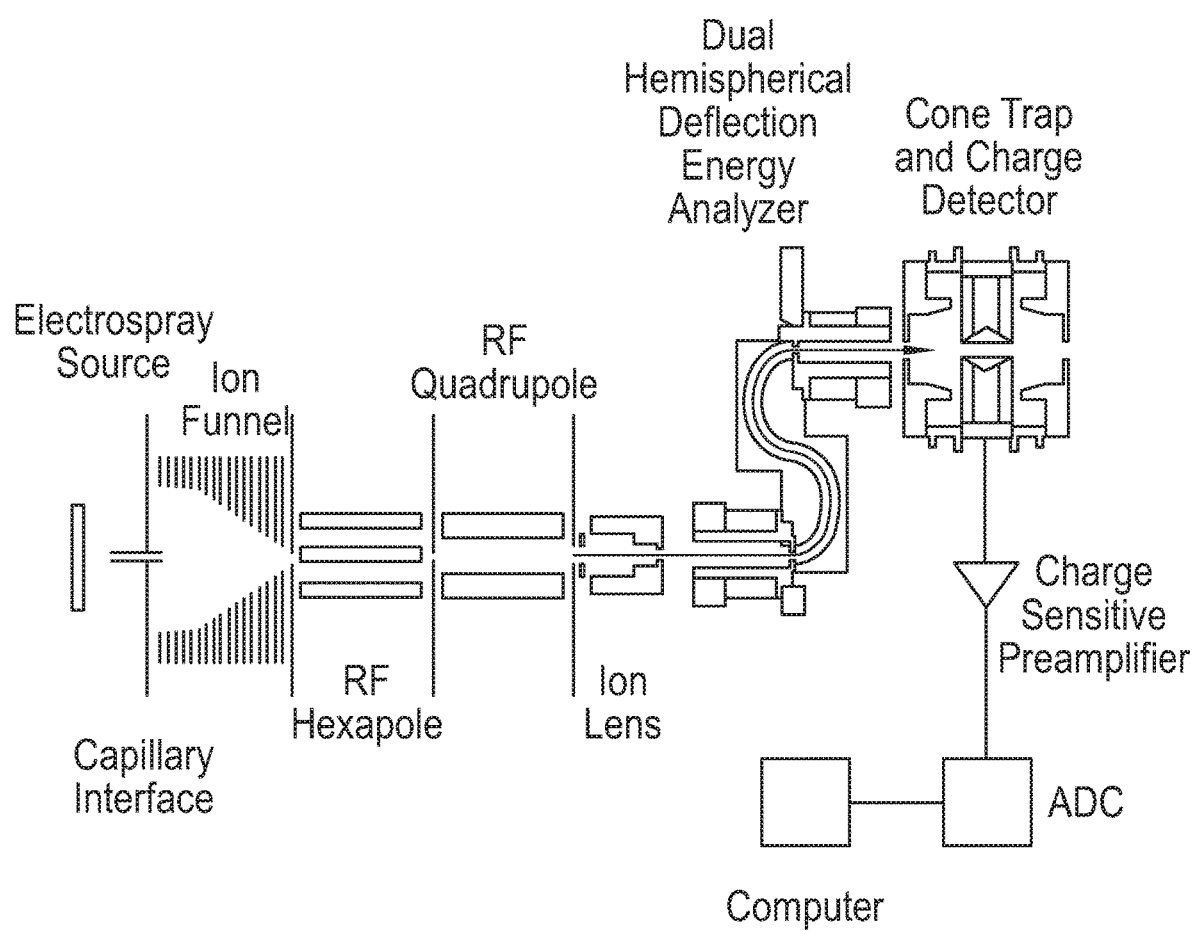
FIG. 3 is a schematic diagram of a charge detection mass spectrometry (CDMS) apparatus used in connection with the present methods.

Referring to FIG. 3, one embodiment of a CDMS apparatus for carrying out the methods of the present disclosure is shown. The lipoprotein standards are ionized via a commercial nanoelectrospray ionization source before entering the charge detection mass spectrometer. Ions enter the instrument through a heated capillary and pass through an RF hexapole, an RF quadrupole, and an ion lens. Ions are energy selected within a dual hemispherical deflection energy analyzer and then focused into a linear ion trap, such as a cone trap, that contains the charge detection cylinder. To initiate a trapping event, a potential is placed on the rear end cap so that ions are reflected back through the trap. After a short delay, a potential is placed on the front end cap to close the trap and cause the ion to oscillate back and forth through the charge detection cylinder. The ion oscillating back and forth through the detection cylinder induces a periodic signal which is amplified, digitized, and then analyzed by a Fortran program using fast Fourier transforms. The m/z is derived from the fundamental frequency and the charge (z) is derived from the magnitude of the fundamental and first harmonic.

In some embodiments, a trapping period in the linear ion trap may be greater than about 10 ms, about 25 ms, about 50 ms, about 75 ms, about 100 ms, about 150 ms, about 200 ms, about 300 ms, about 400 ms, about 3 s, or about 30 s. Additionally, the trapping time may be from about 10 ms to about 1000 ms, about 25 ms to about 1000 ms, about 50 ms to about 1000 ms, about 75 ms to about 1000 ms, about 100 ms to about 1000 ms, about 150 ms to about 1000 ms, about 200 ms to about 1000 ms, or about 300 ms to about 1000 ms.

In some embodiments of the present disclosure, the single particle mass spectrometry can be carried out or performed by time of flight mass spectrometry, charge detection mass spectrometry, quadrupole ion trap mass spectrometry, Fourier transform ion cyclotron resonance and/or Orbitrap mass spectrometry. In some embodiments the single particle mass spectrometry can be carried out or performed with micromechanical/nanomechanical oscillator. These approaches for carrying out single particle mass spectrometry can be employed individually or in any combination.

In some embodiments, single particle mass spectrometry can be carried out or performed on a commercial mass spectrometer retro-fitted for single particle measurements. As one nonlimiting example, a single particle detector can be retrofitted to an existing instrument (e.g., a commercial instrument) that would allow single particle mass measurements to be performed. In one nonlimiting example, the commercial instrument could be a quadrupole time of flight (QTOF) mass spectrometer.

Sample preparation for carrying out the methods of this disclosure may be carried out according to protocols described herein as well as protocols known in the art for conventional mass spectrometry and single particle mass spectrometry methods. Such methods can involve transferring a sample to a solution containing a volatile salt.

In some embodiments, volatile, structure preserving buffers are utilized. In some embodiments, the salt can be ammonium acetate, although other salts may be used in some embodiments. Ammonium acetate may be present in a concentration of about 1 mM to about 15 mM, about 5 mM to about 15 mM, about 10 mM to about 15 mM, about 1 mM to about 12.5 mM, about 5 mM to about 12.5 mM, about 10 mM to about 12.5 mM, about 5 mM to about 10 mM, or about 12.5 mM. In some embodiments, the buffer has a pH of about 7 to about 8 or about 7.5.

In some embodiments, the methods of the present disclosure comprise analyzing lipoproteins obtained from a patient to evaluate the patient's risk for cardiovascular disease. The methods may comprise taking total measures of HDL and LDL to evaluate a patient's risk for cardiovascular disease. The HDL may comprise several subtypes with several subgroups that populate each subtype. Similarly, LDL may comprise of several subtypes. In some embodiments, the methods described herein comprise directly measuring subtypes and/or subgroups within a lipoprotein mixture. Such methods may be utilized to improve risk assessment through characterization and/or identification of particular subgroups.

In some embodiments, tandem mass spectrometry or mass spectrometry/mass spectrometry (MS/MS) techniques may be used to analyze lipoprotein subpopulations. For example, ions with a narrow band of m/z values may be selected using a mass spectrometer, and the ions may be broken into fragments using a variety of methods, such as, collision induced dissociation, collisionally activated dissociation, surface induced dissociation, photo-induced dissociation (including infrared multiple photon dissociation and UV photodissociaton), electron-impact induced dissociation, electron transfer dissociation, and electron capture dissociation. The mass spectrometer may be a time-of-flight mass spectrometer, a quadrupole mass spectrometer, a linear and non-linear ion trap mass spectrometer, a Fourier transform mass spectrometer, a magnetic sector mass spectrometer, a Orbitrap mass spectrometer, a double focusing mass spectrometer, or any other type of mass spectrometer used for conventional mass spectrometry (MS). As discussed further below, CDMS measurements have shown that the lipoprotein populations and subpopulations have a narrow range of m/z values. This allows a specific subpopulation of lipoprotein to be selected using the mass spectrometer and dissociated into fragments that can be analyzed by conventional MS, CDMS, or a combination of both conventional MS and CDMS to identify the components present in the selected lipoprotein subpopulation.

In some embodiments, CDMS may be used in connection with the present methods to analyze a broad range of masses encompassing many lipoprotein classes in a single experiment. For example, CDMS may be employed to characterize lipoproteins directly from plasma without the need for extensive isolation or enhancing the purity of the plasma. It should be appreciated that, in some embodiments, CDMS may be used to analyze whole blood, plasma, or serum to determine abundances of lipoprotein populations (e.g., high-density (HDL), low-density (LDL), and very low-density (VLDL)) and subpopulations. Although whole blood, plasma, and serum are complex mixtures of many different components with widely varying concentrations, lipoprotein populations and subpopulations may be isolated from other components (e.g., proteins) present in the whole blood, plasma, and serum by correlating the charge, mass, and mass-to-charge (m/z) values measured by CDMS. As discussed further below, CDMS measurements have shown that the lipoprotein populations and subpopulations have a range of m/z values.

DEFINITIONS

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

As used herein, the terms "reduce," "reduces," "reduction" and similar terms mean a decrease of at least about 25%, 35%, 50%, 75%, 80%, 85%, 90%, 95%, 97% or more.

As used herein, the terms "enhance," "enhances," "enhancement" and similar terms indicate an increase of at least about 5%, 10%, 20%, 25%, 50%, 75%, 100%, 150%, 200%, 300%, 400%, 500% or more.

Likewise, an "isolated" lipoprotein means a lipoprotein that is at least partially separated from at least some of the other components of the naturally occurring organism. In representative embodiments an "isolated" lipoprotein is enriched by at least about 10-fold, 100-fold, 1000-fold, 10,000-fold or more as compared with the starting material.

As used herein, by "isolate: or "purify" (or grammatical equivalents) a lipoprotein, it is meant that the lipoprotein is at least partially separated from at least some of the other components in the starting material. In representative embodiments an "isolated" or "purified" lipoprotein is enriched by at least about 10-fold, 100-fold, 1000-fold, 10,000-fold or more as compared with the starting material.

Having described the present invention, the same will be explained in greater detail in the following examples, which are included herein for illustration purposes only, and which are not intended to be limiting to the invention.

EXAMPLES

Materials

Low density lipoprotein (LDL), high density lipoprotein (HDL), and HDL subtypes HDL-2 an HDL-3 were purchased from Academy Bio-Medical Company (Houston, Tex., USA). The high density lipoprotein standards were buffer exchanged into 5, 10, or 12.5 mM ammonium acetate ($NH_4OAc$) at pH 7.5 via micro Bio-Spin® columns (Bio-Rad Laboratories, Hercules, Calif., USA). Low density lipoprotein was dialyzed overnight into 12.5 $NH_4OAc$ at pH 7.5. The final concentration of the lipoprotein standards after exchange into $NH_4OAc$ was <1 mg/mL.

The lipoprotein standards were purified via ultracentrifugation and isolated from a range of densities. The HDL standard contained all species within a density range of 1.063-1.210 g/mL The subtypes of HDL, HDL-2 and HDL-3, were isolated from a smaller band of densities of 1.063 to 1.120 g/mL and 1.120 to 1.210 g/mL, respectively.

Instrumentation

The lipoprotein standards were ionized via a commercial nanoelectrospray ionization source before entering a home-built charge detection mass spectrometer described in Contino, N. C., et al., *Int. J. Mass Spectrom.* 2013, 345-347, 153-159; Contino, N. C.; et al., *J. Am. Soc. Mass Spectrom.* 2013, 24, 101-108; Pierson, E. E.; et al., *Int. J. Mass Spectrom.* 2013, 337, 50-56; Pierson, E. E.; et al., *J. Am. Soc. Mass Spectrom.* 2015, 26, 1213-1220; Keifer, D. Z.; et al., *Anal. Chem.* 2015, 87, 10330-10337, incorporated by reference herein. Ions entered the instrument through a heated capillary and were transported through an ion funnel, RF hexapole and RF quadrupole. A DC offset on the hexapole set the nominal ion energy around 100 eV/charge. The ions extracted from the quadrupole were focused into the entrance of the dual hemispherical deflection energy analyzer (HDA). The energy selected ions were then focused into a modified cone trap that contained the charge detection cylinder. To initiate a trapping event, a potential was placed on the rear end cap so that ions were reflected back through the trap. After a short delay, a potential was placed on the front end cap to close the trap and caused the ion to oscillate back and forth through the charge detection cylinder. A trapping period of 100 ms was employed, after which the trap was opened (both end caps set to ground) and the trapping cycle repeated. The ion oscillating back and forth through the detection cylinder induced a periodic signal which was amplified, digitized, and then analyzed by a Fortran program using fast Fourier transforms. The m/z was derived from the fundamental frequency and the charge (z) was derived from the magnitude of the fundamental and first harmonic.

Results

Figure 1B:
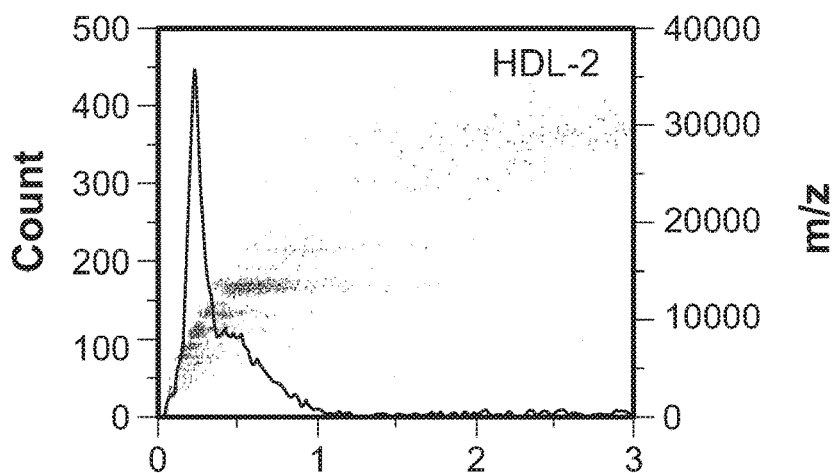
FIG. 1B is a mass spectrum for HDL-2 overlaid with a scatter plot of m/z versus mass where each point represents a single ion.
Figure 1C:
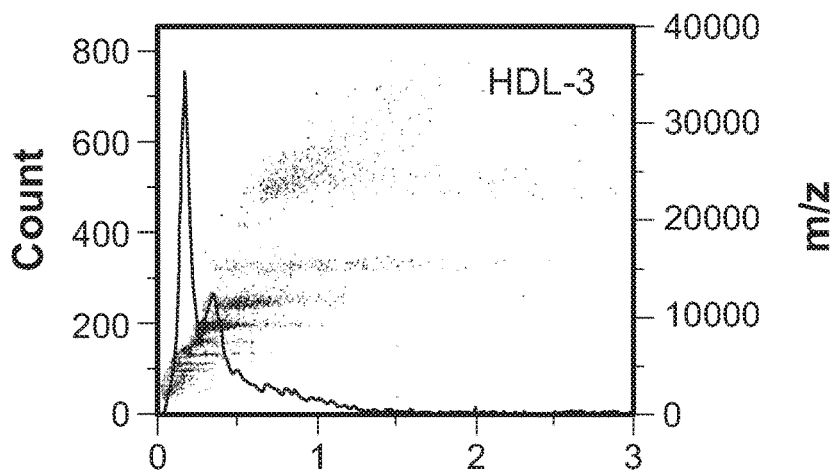
FIG. 1C is a mass spectrum for HDL-3 overlaid with a scatter plot of m/z versus mass where each point represents a single ion.

FIGS. 1A-1C show the mass spectra recorded for HDL, subtype HDL-2, and subtype HDL-3, respectively. Overlaid on each mass spectrum is a scatter plot of m/z (right hand axis) versus mass where each point represents a single ion. In CDMS, the m/z and mass of individual ions can be directly correlated. Clusters of points represent ions that share similar m/z values which correspond to particular populations within same subtype that have slightly different stoichiometry.

The mass spectrum for isolated HDL is shown in FIG. 1A. The most prominent peak in the mass spectrum was centered at 229 kDa and showed a high mass tail that extended up to 1 MDa. Ions were detected out to 3 MDa, albeit in low abundance. Without intending to be bound by theory, the CDMS peak shape was expected to be Gaussian with a width determined by the uncertainties in the m/z and charge measurements. For a homogenous population of only a single species, the expected peak width for the main feature in the mass spectrum would be 17.8 kDa. Instead, the full width at half maximum measured 138 kDa, indicating the peak was made up of contributions from many species. The overlaid scatter plot (right hand axis) showed at least four densely populated clusters at well-defined m/z values of 6.60, 7.50, 8.90, and 10.7 kTh. The center masses for each subpopulation were determined by isolating the ions in each cluster, binning the masses into a histogram, and then fitting the histogram with a Gaussian. Although the ions are well separated by m/z, the four clusters of ions differed only slightly in mass, corresponding to masses of 165, 200, 250 and 376 kDa, respectively.

FIG. 1B illustrates the mass spectrum for subtype HDL-2. The most abundant feature in the mass spectrum was a peak centered at 238 kDa. A high mass shoulder is present starting around 0.5 MDa and extended toward 1 MDa in mass. A low abundant continuum of ions was observed out to 3 MDa. Noise did not contribute to the low abundant ion counts observed at masses above 1 MDA as empty, partial, and multiple ion trapping events were discarded during data analysis. All ion intensity reported in the mass spectrum were from real ions that had been trapped for the entire duration of the 100 ms trapping event. The overlaid scatter plot displaying the relationship of m/z versus mass for each ion showed evidence of at least six distinct subpopulations with m/z below 20 kTh. Three densely populated clusters at m/z 6.6, 7.5, and 8.8 kTh contributed to the most abundant feature in the mass spectrum and correspond to masses of 161, 197, and 239 kDa, respectively. Two additional clusters at 10.1 and 13.4 kTh appeared to contribute to the high mass shoulder with the center of masses at 326 and 550 kDa, respectively.

FIG. 1C illustrates the mass spectrum for the smallest of the high density lipoprotein subtypes, HDL-3. There were two distinct features observed in the mass spectrum: a high intensity peak centered at 170 kDa and a smaller and a lower abundant feature centered at 340 kDa. The ion counts diminished as masses reached 2 MDa. Very few ions were present above 2 MDa. Eight distinct clusters were observed in the overlaid scatter plot. The four clusters that contained the majority of the total ion intensity were in the low m/z regime positioned at 5.8, 6.8, 7.7, and 9.5 kTh. These clusters correspond to populations with masses of 138, 175, 213, and 342 kDa, respectively. The additional high m/z clusters at 11.5, 15.0, and 25.0 kTh correspond to high mass particles centered around 0.5, 0.9, and 1.1 MDa and were responsible for the broad but low-abundant distribution of masses that followed the 340 kDa peak in the mass spectrum.

Each subtype, HDL-2 and HDL-3, overlapped in density with the HDL sample, therefore, it is expected that similar subpopulations were observed among the three standards. Specifically, HDL and HDL-2 shared two clusters of ions centered around m/z values of 6.5 and 7.5 kTh corresponding to particles having masses of 165 and 200 kDa, respectively. Without intending to be bound by theory, although the exact stoichiometry is unknown, it is likely that these two clusters were of the same subpopulation in both isolated samples.

The subpopulations with masses of 175, 212, and 342 kDa in FIG. 1C agree with values estimated from literature and are tentatively assigned to subpopulations of HDL-3a, HDL-3b, and HDL-3c, respectively. The masses observed for HDL and HDL-2 subpopulations in FIGS. 1A and 1B do not directly conform to particles of known stoichiometry. Currently, more than 10 HDL subspecies have been identified and are classified by pre-beta and pre-alpha type particles. Without intending to be bound by theory, it is possible that an assortment of small, medium, and large HDL particles as well as pre-beta and pre-alpha subspecies were observed by CDMS.

Figure 2:
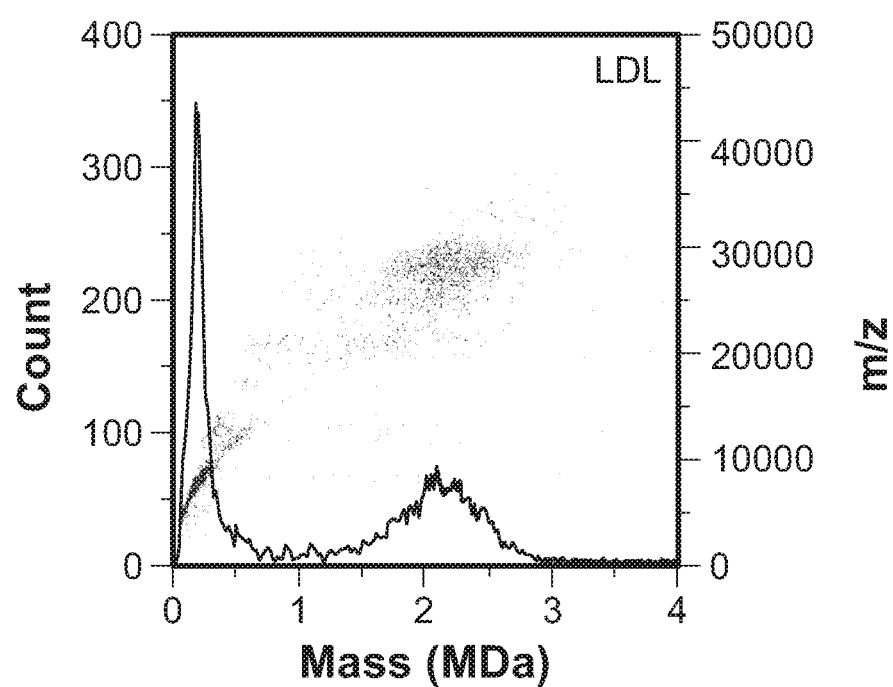
FIG. 2 is a mass spectrum for LDL overlaid with a scatter plot of m/z versus mass where each point represents a single ion.

The LDL mass spectrum in FIG. 2 showed a high abundant peak at approximately 200 kDa followed by a broad distribution of ions centered around 2.14 MDa. The overlaid scatter plot showed that the ions contributing to the 200 kDa peak spanned a range of 5 to 10 kTh with no discernible clusters, as were observed in the HDL standards. The ions with masses centered at 2.14 MDa showed a more disperse distribution of ions with m/z values ranging from 18 to 38 kTh and having a mean value of 27 kTh. Without intending to be bound by theory, it is likely the highly disperse range of masses and m/z values for LDL were due to differing amounts of lipid and cholesterol cargo. There is evidence for small, high density LDL where presence is expected to be a biomarker for coronary artery disease. Ions with masses 0.5 to 2 MDa are tentatively assigned to the more dense subspecies of LDL.

In addition, a high intensity peak was observed in the LDL standard near 200 kDa. Because the structural protein of LDL apolipoprotein B-100 weighs in at approximately 550 kDa, the intense low mass peak is attributed to contamination from HDL that may have occurred during the isolation process.

With the direct measurement of mass and known density, the particle diameters of each subtype and subpopulations were estimated. The particle diameters were in good agreement with those particle diameters in literature, reporting diameters of 7-12, 9.2-10.2, 7.5-8.8 and 21-27 nm for HDL, HDL-2, HDL-3, and LDL, respectively. Although some of the species observed in HDL-2 had diameters below 7 nm, those particles can be attributed to overlap from HDL particles in the isolation process.

Figure 4A:
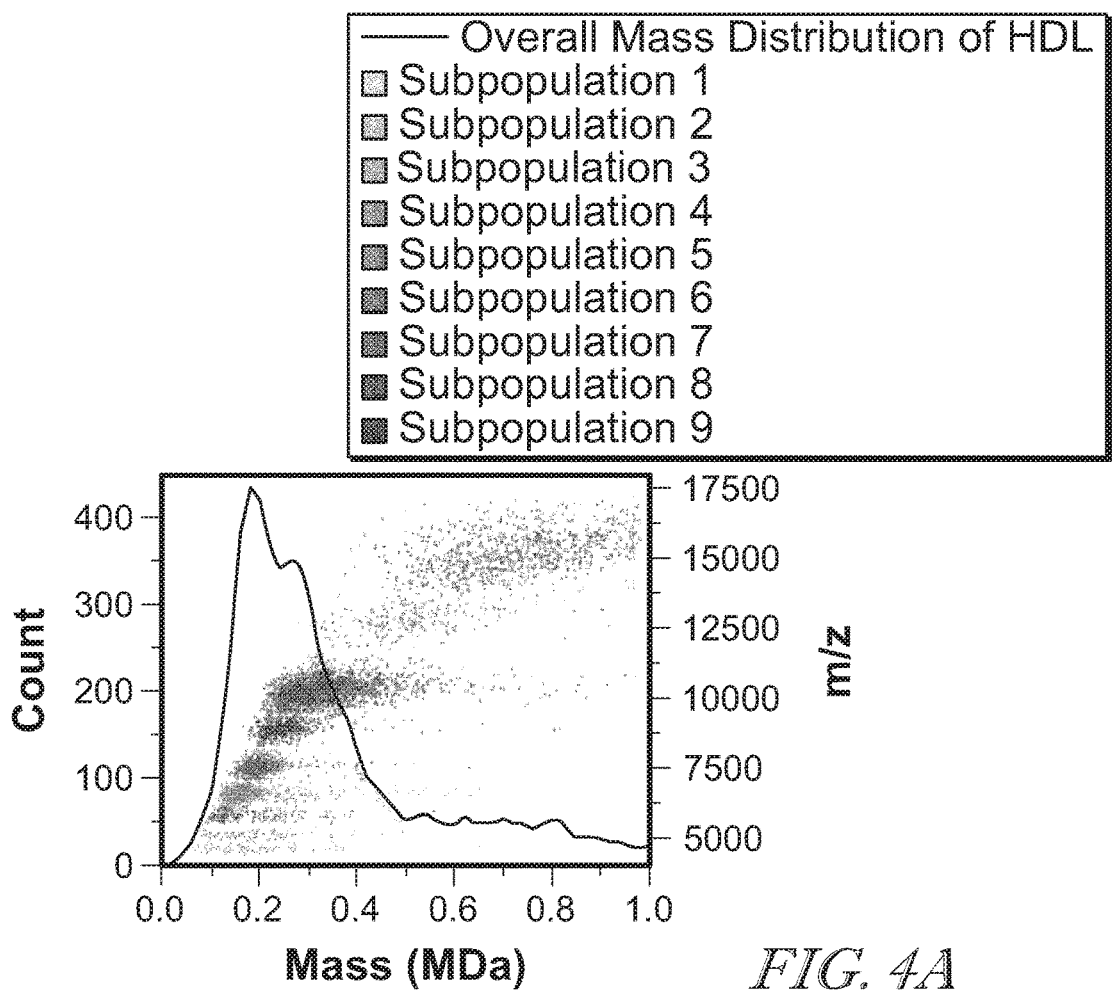
FIG. 4A is a mass spectrum measured for HDL overlaid with a scatter plot of m/z versus mass where each point represents a single ion. HDL subclasses are resolved in the scatterplot.
Figure 4B:
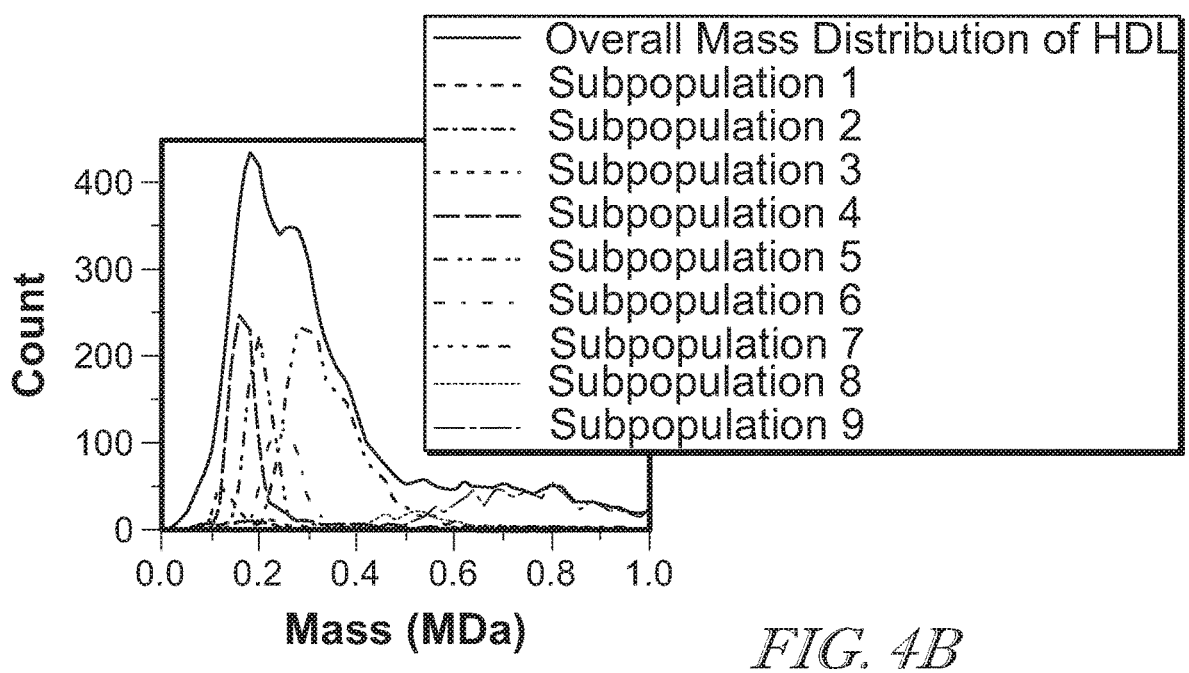
FIG. 4B illustrates a mass distribution for HDL identical to that shown in FIG. 4A along with mass distributions for the HDL subpopulations identified in the scatterplot of m/z versus mass in FIG. 4A.

FIG. 4A illustrates a CDMS spectrum measured for an HDL sample where seven subpopulations have been identified in the scatter plot of m/z versus mass. In FIG. 4B, the mass distributions of the subpopulations identified in FIG. 4A are plotted along with the overall mass distribution of this HDL sample. The mass distributions for the subpopulations can be accounted for by HDL particles with different numbers of the key structural proteins Apolipoprotein A-1 (Apo A-I) and Apolipoprotein A-II (Apo A-II) as described by Lutomski, Gordon, Remaley, and Jarrold ("Resolution of Lipoprotein Subclasses by Charge Detection Mass Spectrometry", Anal. Chem. 2018, 90, 6353-6356. DOI: 10.1021/ acs.analchem.8b01127; the entire contents of which are incorporated by reference herein).

As discussed above, given that HDL is around 50% protein and that the two major structural proteins Apo A-I (28,081 Da) and Apo A-II (17,252 Da) together contribute around 90% of the total protein, a particle with $n_I$ Apo A-I proteins and $n_{II}$ Apo A-II proteins would be expected to have a mass (in kDa) of around $$m(n_I, n_{II}) = (28.081 \times n_I + 17.252 \times n_{II})/0.45 \quad (1)$$

Figure 4C:
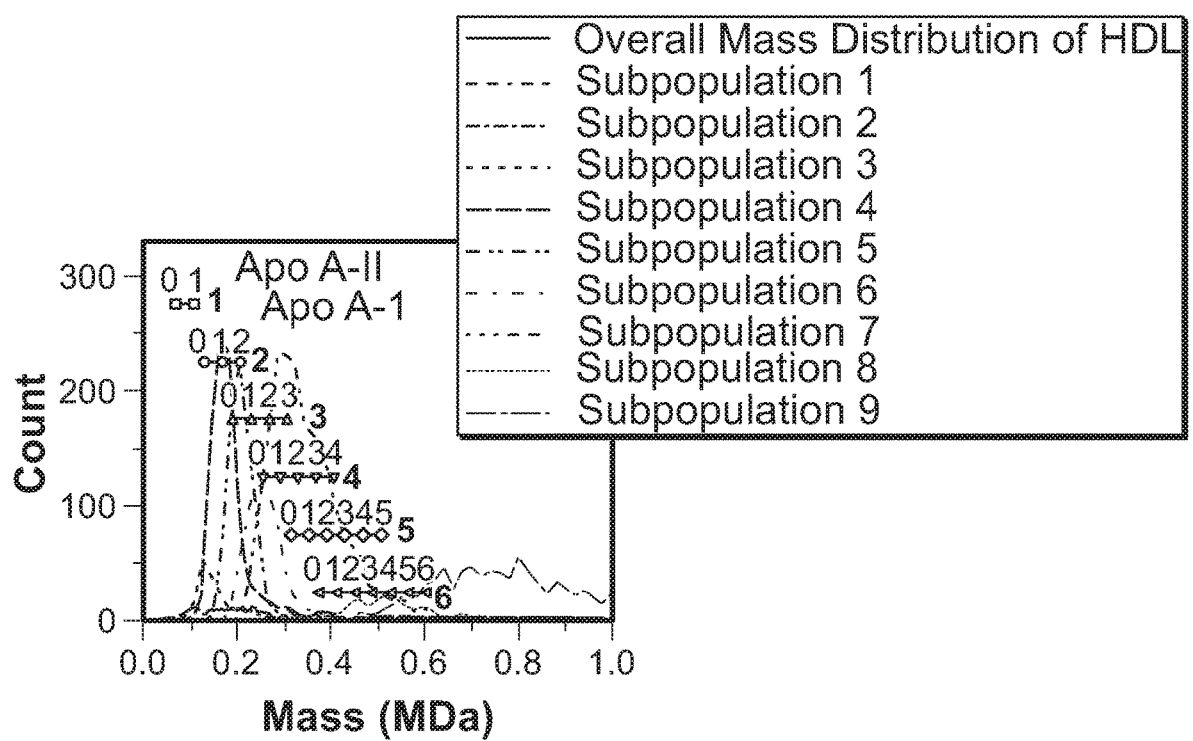
FIG. 4C illustrates mass distributions for the HDL subpopulations overlaid with scales giving approximate masses for HDL particles with $n_I$ copies of Apolipoprotein A-I and $n_{II}$ copies of Apolipoprotein A-II, wherein the large digits represent the number of Apo A-I and the small digits represent the number of Apo A-II.

Masses predicted by Equation 1 are shown by the scales in FIG. 4C. The large digits give the number of Apo A-I proteins, with $n_I$ ranging from 1 to 6. The smaller digits give the number of Apo A-II proteins, with $n_{II}$ ranging from zero to $n_{II} \leq n_I$. The points on the scales give the masses from Equation 1 for specific combinations of $n_I$ and $n_{II}$. For example, for $n_I=1$ and $n_{II}=2$, the expected mass from Equation 1 is 163 kDa. A distribution of masses is expected for each $n_I, n_{II}$ combination, and the masses given by Equation 1 are only approximate. However, they provide a starting point for assigning the subpopulations resolved in FIGS. 4A and 4B. For $n_I=2$, there are points on the scale in FIG. 4C at 125, 163, and 201 kDa corresponding to $n_{II}=0$, 1, and 2. These match up with the three lowest mass components in FIGS. 4B and 4C (which have average masses of 129/126, 165/163, and 200/208 kDa). The resolving power degrades as the mass increases so peaks due to different $n_{II}$ are not expected to be resolved for higher masses. The resolved component centered on around 250/261 kDa in FIGS. 4B and 4C can be attributed to $n_I=3$ and $n_{II}=1$-2. Similarly, the peak at 321/327 kDa can be attributed to $=4$ and $n_{II}=1$-3. Particles with $n_I=5$ and 6 may contribute to the high mass tail on the 321-327 kDa peak and to the 511/463 kDa peak. The highest mass component in FIG. 4 at 756 kDa is large for an HDL particle. A proteomics study of the HDL sample revealed the presence of Apo B100, the main structural protein of LDL. Thus, an LDL impurity may be responsible for some of the high mass component observed in the HDL spectrum.

Figure 5:
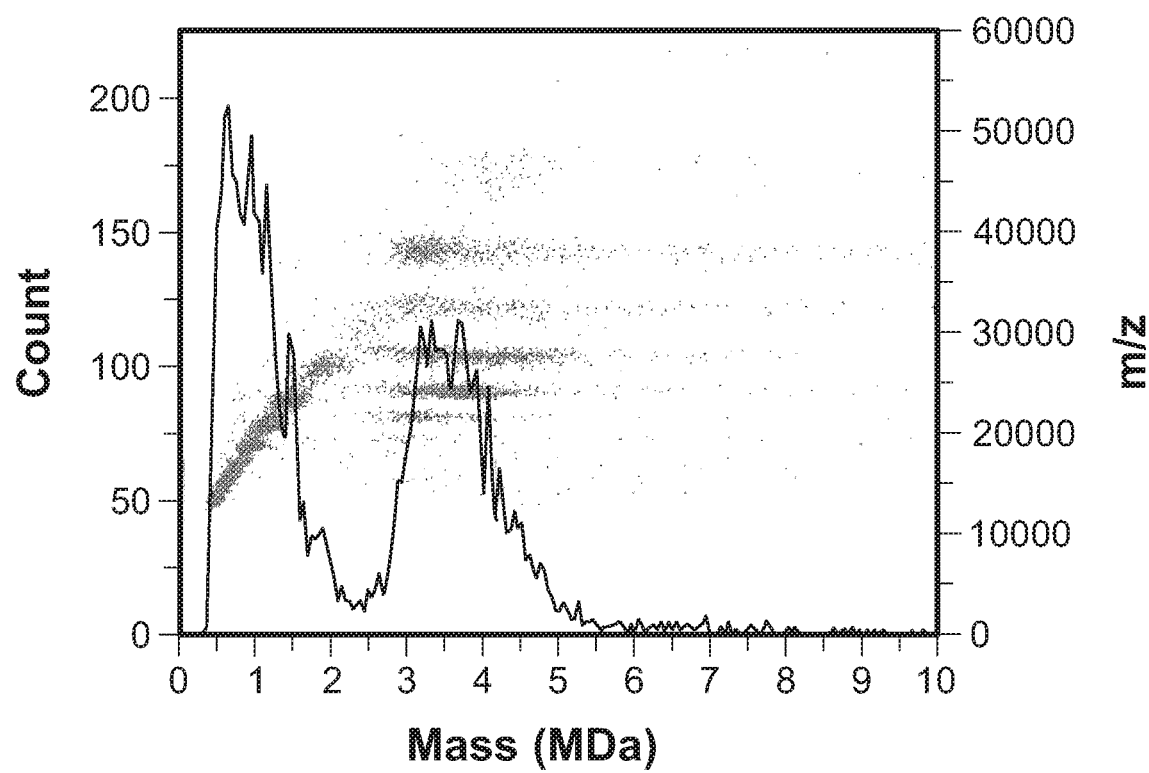
FIG. 5 illustrates a mass spectrum measured for LDL overlaid with a scatter plot of m/z versus mass where each point represents a single ion. Subpopulations of LDL are resolved in the scatterplot. Note that these subpopulations have overlapping mass distributions.

FIG. 5 illustrates a mass spectrum measured for LDL which shows the resolution of subclasses in the scatter plot of an LDL sample. In contrast to HDL, where the subclasses have partly discrete mass distributions, the subclasses of LDL have broad and overlapping mass distributions.

What is claimed:

1. A method of identifying a density class of intact lipoprotein particles present in a sample containing multiple density classes of intact lipoprotein particles, the method comprising:
    a) producing lipoprotein ions from the multiple density classes of intact lipoprotein particles contained in the sample;
    b) subjecting the lipoprotein ions to single-particle mass spectrometry to determine a respective mass of each of the lipoprotein ions; and
    c) identifying the density class of intact lipoprotein particles based on the determined masses of the lipoprotein ions.

2. The method of claim 1, wherein subjecting the lipoprotein ions to single-particle mass spectrometry comprises, for each of the lipoprotein ions, (i) measuring a mass-to-charge ratio of the ion, (ii) measuring a charge of the ion, and (iii) determining the mass of the ion based on the measured mass-to-charge ratio and the measured charge of the ion, and wherein the charge of the ion and the mass-to-charge ratio of the ion are measured simultaneously.

3. The method of claim 1, wherein the single-particle mass spectrometry comprises charge detection mass spectrometry.

4. The method of claim 3, wherein the charge detection mass spectrometry comprises, for each of the lipoprotein ions, focusing the ion into a linear ion trap, the linear ion trap comprising a charge detection cylinder.

5. The method of claim 4, wherein the mass-to-charge ratio of the ion is measured based on a time period that the ion takes to traverse the charge detection cylinder or the fundamental frequency at which the ion oscillates in the charge detection cylinder.

6. The method of claim 4, wherein the charge of the ion is measured based on the amplitude of a signal due to the ion oscillating in the charge detection cylinder.

7. The method of claim 4, wherein the ion is trapped in the linear ion trap for a trapping period to determine the mass to charge ratio of the ion.

8. The method of claim 1, wherein the masses of the lipoprotein ions range between about 100 kDa to about 80 MDa.

9. The method of claim 1, wherein subjecting the lipoprotein ions to single-particle mass spectrometry comprises, for each of the lipoprotein ions, (i) measuring simultaneously a mass-to-charge ratio of the ion and a charge of the ion, and (ii) determining the mass of the ion based on the measured mass-to-charge ratio and the measured charge of the ion,
    and wherein the method further comprises correlating the measured mass-to-charge ratios and the corresponding determined masses of the lipoprotein ions to distinguish between different subtypes or subpopulations of the lipoprotein ions within at least one of the multiple density classes of intact lipoprotein particles contained in the sample.

10. The method of claim 9, wherein the different subtypes of the lipoprotein ions include different subtypes of the at least one of the multiple density classes of intact lipoprotein particles and the different subpopulations of the lipoprotein ions include different subpopulations of at least one of the subtypes or of at least one of the multiple density classes of intact lipoprotein particles.

11. The method of claim 10, wherein one of the multiple density classes of intact lipoprotein particles contained in the sample is intact high-density lipoprotein (HDL) particles,
    and wherein the different subtypes of the lipoprotein ions include at least one subtype of the HDL particles, and the subpopulations include different subpopulations of the HDL particles or subpopulations of the at least one subtype of the HDL particles.

12. The method of claim 1, wherein subjecting the lipoprotein ions to single-particle mass spectrometry comprises, for each of the lipoprotein ions, (i) measuring simultaneously a mass-to-charge ratio of the ion and a charge of the ion, and (ii) determining the mass of the ion based on the measured mass-to-charge ratio and the measured charge of the ion, and wherein the method further comprises correlating the measured mass-to-charge ratios, the corresponding measured charges and the corresponding determined masses of the lipoprotein ions to distinguish between different subtypes or subpopulations of the lipoprotein ions within at least one of the multiple density classes of intact lipoprotein particles contained in the sample.

13. A method of identifying subtypes of a density class of intact lipoprotein particles present in a sample containing the density class of intact lipoprotein particles, the method comprising:
   a) producing lipoprotein ions from the density class of intact lipoprotein particles contained in the sample;
   b) simultaneously measuring a charge and a mass-to-charge ratio of each of the lipoprotein ions;
   c) determining a mass of each of the lipoprotein ions based on the measured charge and mass-to-charge ratio values thereof; and
   d) identifying the subtypes of the density class of intact lipoprotein particles based on the determined masses and measured charges of the lipoprotein ions.

14. The method of claim 13, further comprising (f) identifying subpopulations of at least one of the identified subtypes of the density class of intact lipoprotein particles based on the determined masses and measured charges of the lipoprotein ions.

15. A method of identifying subpopulations of a density class, or subtype of a density class, of intact lipoprotein particles present in a sample containing the density class, or subtype of the density class, of intact lipoprotein particles, the method comprising:
   a) producing lipoprotein ions from the density class, or the subtype of the density class, of intact lipoprotein particles contained in the sample;
   b) simultaneously measuring a charge and a mass-to-charge ratio of each of the lipoprotein ions;
   c) determining a mass of each of the lipoprotein ions based on the measured charge and mass-to-charge ratio values thereof; and
   d) identifying the subpopulations of the density class, or the subtype of the density class, of intact lipoprotein particles based on the determined masses and measured charges of the lipoprotein ions.

* * * * *

UNITED STATES PATENT AND TRADEMARK OFFICE
CERTIFICATE OF CORRECTION

| | | |
|---|---|---|
| PATENT NO. | : 11,668,719 B2 | Page 1 of 1 |
| APPLICATION NO. | : 16/647955 | |
| DATED | : June 6, 2023 | |
| INVENTOR(S) | : Martin F. Jarrold et al. | |

It is certified that error appears in the above-identified patent and that said Letters Patent is hereby corrected as shown below:

On the Title Page

Item (72), should read:
Martin F. Jarrold, Bloomington, IN (US); Corinne A. Lutomski, Bloomington, IN (US)

Signed and Sealed this
Sixth Day of August, 2024

Katherine Kelly Vidal
*Director of the United States Patent and Trademark Office*